United States Patent [19]

Andreoli et al.

[11] Patent Number: 4,476,319

[45] Date of Patent: Oct. 9, 1984

[54] P-CHLOROPHENOXYACETIC ACID DERIVATIVE, ITS METHOD OF PREPARATION, THE PHARMACEUTICAL COMPOSITIONS CONTAINING IT AND ITS USE IN MEDICINE

[75] Inventors: Romeo R. Andreoli; Xavier D. Cirera, both of Barcelona, Spain

[73] Assignee: Sociedad Espanola de Especialidades Farmaco-Terapeuticas S.A., Barcelona, Spain

[21] Appl. No.: 436,960

[22] Filed: Oct. 27, 1982

[30] Foreign Application Priority Data

Oct. 29, 1981 [ES] Spain .................................... 506.669

[51] Int. Cl.$^3$ ............................................. C07C 69/76
[52] U.S. Cl. ..................................... 560/62; 424/308; 424/309
[58] Field of Search ................... 560/62; 424/308, 309

[56] References Cited

U.S. PATENT DOCUMENTS 2,628,973  2/1953  Cusic .................................... 560/62
3,546,273  12/1970  Bolhofer ............................... 560/62

FOREIGN PATENT DOCUMENTS 50-19541  7/1975  Japan .................................... 560/62
50-19542  7/1975  Japan .................................... 560/62

Primary Examiner—Paul J. Killos
Attorney, Agent, or Firm—Michael J. Striker

[57] ABSTRACT

A new compound derived from p-chlorophenoxyacetic acid, the p-chlorophenoxyacetate of 1-aminoadamantine-2-ethanol of the following structural formula I:

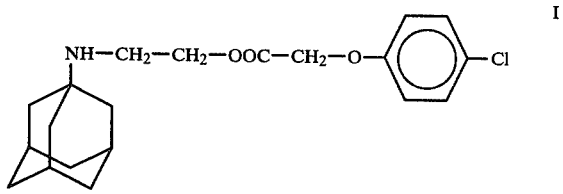

as well as its pharmaceutically acceptable salts, possessing properties for the treatment of various pathological conditions of the central nervous system. Also disclosed are its method of preparation; pharmaceutical compositions containing the said compounds; and the treatment of various pathological conditions of the central nervous system with the use of the said compositions.

7 Claims, No Drawings

P-CHLOROPHENOXYACETIC ACID DERIVATIVE, ITS METHOD OF PREPARATION, THE PHARMACEUTICAL COMPOSITIONS CONTAINING IT AND ITS USE IN MEDICINE

The present invention concerns a new compound derived from p-chlorophenoxyacetic acid, the p-chlorophenoxyacetate of 1-aminoadamantine-2-ethanol of structural formula I

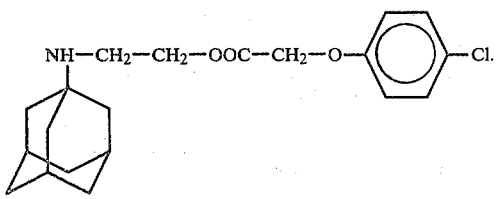

The scope of the present invention also embraces the salts thereof, which are of pharmacological interest; its method of preparation; the pharmaceutical compositions containing it; and its therapeutic applications.

The compound I and its salts are new agents which are active on the central nervous system, being of use in the treatment of various pathological conditions of the system.

The conditions for which the new p-chlorophenoxyacetic acid derivatives are recommended include:

Neuropsychic asthenia; problems of attention; memory defects; difficulty in learning; disorders in the capacity for mental concentration; mental involution in senility; amnesia; assistance in the treatment of Parkinson's disease; physical and mental debility; a propensity to a state of depression; irritability and lack of social adaptation due to depression; neuronal hypoxia; cerebral metabolism inadequacies; acute vascular complications; nervous sequelae to cerebral circulatory disorders; vascular, toxic and traumatic comas; and cerebral atherosclerosis.

The active agents according to the present invention may be administered in any of the pharmaceutically typical modes of administration such as tablets, pills, dragees, capsules, injectable solutions and the like, including, but not limited to, the following examples:

Tablets of 50-500 mg of active principle, taken from 2 to 8 times a day.

Syrups of 10 to 200 mg/ml of active principle.

To prepare the p-chlorophenoxyacetate of 1-aminoadamantine-2-ethanol according to the present invention, the esterification reaction is carried out between the acylic compound of the following structural formula II

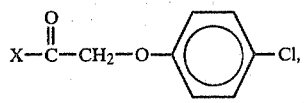

wherein X can be an OH group or a halogen atom (Cl or Br), and the 1-aminoadamantine-2-ethanol of the structural formula III

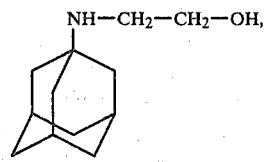

in a suitable inert solvent.

The salts of the compound I are obtained by the same procedure, noting that in order to finalize the reaction, the resulting product is treated with the stoichiometric quantity of the acid in question (hydrochloric, sulphuric, tartaric, etc.)

The novel features which are considered as characteristic for the invention are set forth in particular in the appended claims. The invention itself, however, both as to its construction and its method of operation, together with additional objects and advantages thereof, will be best understood from the following description of specific embodiments.

DESCRIPTION OF THE PREFERRED EMBODIMENTS

Some examples of the method of preparation of the compounds of formula I are detailed below. All such details that are not essential to the invention are considered variables and not limitative thereto.

EXAMPLE 1

Preparation of the p-chlorophenoxyacetate of 1-aminoadamantine-2-ethanol, starting from a p-chlorophenoxyacetic acid halide 22 g (0.11 mol) of 1-aminoadamantine-2-ethanol dissolved in 250 ml of benzene are poured into a 500 ml flask fitted with a mechanical stirrer, using a decanting funnel. 23 g (0.11 m) of p-chlorophenoxyacetyl chloride are added in drops while stirring, the mixture then being stirred for 30 minutes. 120 ml of a 10% solution of sodium carbonate is then added, and the resulting mixture is stirred for 10 minutes. The organic phase is decanted, and the benzene is then removed by distillation. The residue is crystallized with petroleum ether. This yields 37 g (93%) of a white solid.

Elemental analysis: Calculated: C 66.01; H 7.15; Cl 9.77; N 3.85. Found: C 66.2; H 7.05; Cl 9.68; N 3.78.

EXAMPLE 2

Preparation of the p-chlorophenoxyacetate of 1-aminoadamantine-2-ethanol, starting from p-chlorophenoxyacetic acid In a 1 liter flask, provided with a Dean-Stark separator tube and reflux refrigerant, a mixture of 20.5 g (0.011 m) of p-chlorophenoxyacetic acid, 22 g (0.11 m) of 1-aminoadamantine-2-ethanol, 98 g of conc. sulphuric acid and 700 ml of toluene is heated to boiling point over a period of 24 hours. At the end of this period, the mixture is treated with an acqueous solution of 5% sodium carbonate to an alkali pH, and is then washed with water. The mixture is then dried on anhydrous sodium sulphate, and the toluene is removed by distillation at reduced pressure. The crude product so obtained is crystallized with petroleum ether. The yield is 35.2 g (88%) of a white solid.

Elemental analysis: Calculated: C 66.02; H 7.15; Cl 9.77; N 3.85. Found: C 66.1; H 7.10; Cl 9.75; N 3.80.

EXAMPLE 3

Preparation of the chlorhydrate of p-chlorophenoxyacetate of 1-aminoadamantine-2-ethanol A solution of 60 g (0.16 m) of p-chlorophenoxyacetate of 1-aminoadamantine-2-ethanol in 300 ml of ether is subjected to the passage of HCl gas until the precipitation of a solid product is completed. It is left to cool in a refrigerator over a period of 6 hours and it is then filtered. The resulting solid is recrystallized with a mixture of ether and methanol. 61 g (92%) of the product are obtained.

Elemental analysis: Calculated: C 60.00; H 6.75; Cl 17.75; N 3.50. Found: C 60.2; H 6.70; Cl 17.8; N 3.55.

In a similar manner and by using the stoichiometric quantities of the acid in question, the following salts are obtained.

| EXAMPLE | SALT | ELEMENTAL ANALYSIS Calculated | Found |
|---|---|---|---|
| 4 | Sulphate | C: 52.00 | C: 52.1 |
|   |   | H: 6.07 | H: 6.11 |
|   |   | Cl: 7.69 | Cl: 7.65 |
|   |   | N: 3.03 | N: 3.1 |
|   |   | S: 6.93 | S: 6.89 |
| 5 | Tartrate | C: 56.1 | C: 56.3 |
|   |   | H: 6.23 | H: 6.19 |
|   |   | Cl: 6.91 | Cl: 6.88 |
|   |   | N: 2.73 | N: 2.75 |
| 6 | Phosphate | C: 52.00 | C: 52.3 |
|   |   | H: 6.28 | H: 6.31 |
|   |   | Cl: 7.69 | Cl: 7.70 |
|   |   | N: 3.03 | N: 3.0 |
|   |   | P: 6.72 | P: 6.80 |

The following pharmacological activities have been evalulated:

Nootropa activity

Tests were carried out on rats using the technique estimating the loss of memory induced by electric shock, the loss of memory being determined as related to the number of errors made in seeking the outlet from an acquatic labyrinth (Giurgea C. J. Pharmacol (Paris) 3, 1, 17, *1972).

The compound I according to the present invention showed itself to be notably active, giving a 46.5% protection against the loss of memory, as is shown in the Table 1, hereunder.

Activity on learning

This activity was studied by the test of learning in the acquatic labyrinth (Giurgea C. J. Pharmacol (Paris) 3, 1, 17 (1972), the learning resulting in a decrease in the errors made and the time spent in reaching the exit. In another learning test (conditioning cage) the animals placed in the cage receive an electric shock, wich can be avoided by passing from one cell to another. Sara, S. J. and Col. Psychopharmacol (ber.) 25, 32, (1972). The compound I has resulted in an increased learning facility as may be seen in the Table 1.

Anti-depressant activity

This activity was evaluated by the method of examining the desperation behavior in mice (Porsalt, T. D., Arch. Int Pharmacodyn 229, 327 (1977).

A state of despair was induced by placing the animal in a cylinder containing water, and from which escape was impossible, the animal then finding itself obliged to treadmill continually. After a period of vigorous activity, the mouse assumes a characteristic immobile posture, which behavior is capable of reduction by the use of various types of pharmaceutical anti-depressants. It was shown that the administration of the compound I resulted in moderate anti-depressant effects, as is shown in the Table I.

Anti-cataleptic activity

This activity was the subject of Morpurgo tests (Arch. Int. Pharmacodyn, 137, 84 (1962), based on antagonizing the cataleptic condition in rats, induced by fluphenazine.

The compound I slightly reduced the cataleptic activity of the fluphenazine, as is shown in the Table I.

TABLE 1

Results of the pharmacological activity of Compound I:

| TEST | PARAMETER | EVALUATION |
|---|---|---|
| Nootropa activity | Protection from memory loss due to electric shock. (number of errors) | 46.5% $p < 0.01$ |
|   | Decrease with respect to the control in the errors made in the acquatic labrinth. (5th day) | 51.6% $p < 0.01$ |
| Learning activity | Increase with respect to the control in the conditioning cage. (learning) facility) | 14.4% $p < 0.001$ |
| Anti-depressant activity | Protection with respect to the control. | 45.9% $p < 0.001$ |
| Anti-cataleptic activity | Protection against catalepsy by fluphenazine | 25.6% $p < 0.01$ |

Toxicity of the compound I according to the present invention is determined using the Irwin or "screening" multi-dimensional test (Phsychopharmacologia (Berl), 13, 222–257 (1968). There was no evidence as to effects of non-toxic doses. Toxic doses caused death accompanied by trembling and clonic convulsions.

The $LD_{50}$ of the compound I in the rat and the mouse is shown in the following table:

| ANIMAL | RAT | | MOUSE | |
|---|---|---|---|---|
| Route | i.p. | p.o. | i.p. | p.o. |
| $LD_{50}$ value mg/kg | 360 | >4000 | 415 | >4000 |

(i.p. = intraperitoneal route; p.o. = oral route)

It will be understood that each of the elements described above, or two or more together, may also find a useful application in other types of compounds differing from the types described above.

While the invention has been illustrated and described as embodied in a p-chlorophenoxyacetic acid derivative, its method of preparation, the pharmaceutical compositions containing it and its use in human medicine, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

We claim:

1. P-chlorophenoxyacetate of 1-aminoadamantine-2-ethanol, of the following structural formula I:

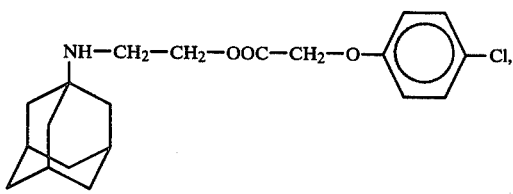

derived from p-chlorophenoxy acetic acid, as well as its pharmaceutically acceptable salts.

2. Method of preparation of the compound of general formula I according to claim 1, comprising esterifying an acylic compound of the following structural formula II:

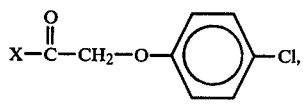

in which X is an OH group or a halogen atom, and 1-aminoadamantine-2-ethanol of the following structural formula III:

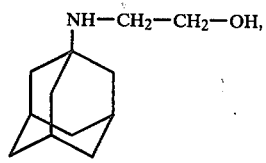

in a suitable inert solvent.

3. The method according to claim 2, wherein said halogen atom is chlorine or bromine.

4. The method according to claim 2, further comprising to obtain the salts of the compound of formula I, treating the compound of formula I with the stoichiometric quantity of an acid.

5. The method according to claim 4, wherein said acid is hydrochloric, sulphuric, or tartaric acid.

6. A pharmaceutical composition useful for the treatment of pathological conditions of the central nervous system, comprising as active ingredient the compound derived from the p-chlorophenoxyacetic acid of the structural formula I according to claim 1, in a suitable pharmaceutical vehicle.

7. The pharmaceutical composition in accordance with claim 6, for use in the treatment of Neuropsychic asthenia, difficulty in learning, disorders in the capacity for mental concentration, mental involution in senility, amnesia, Parkinson's disease, physical and mental debility, propensity to a state of depression, irritability and problems in social adaptation due to depression, neuronal hypoxia, cerebral metabolism inadequacies, acute vascular complications, nervous sequelae to cerebral circulatory disorders, vascular, toxic or traumatic comas, comas in general, and cerebral atherosclerosis.

* * * * *